United States Patent
Koestner et al.

(10) Patent No.: US 8,426,637 B2
(45) Date of Patent: Apr. 23, 2013

(54) PROCESS FOR PREPARATION OF HIGH PURITY METHACRYLIC ACID

(75) Inventors: Martin Koestner, Darmstadt (DE); Gerhard Koelbl, Gernsheim (DE); Ralf Meier, Dortmund (DE)

(73) Assignee: Evonik Röhm GmbH, Darmstadt (DE)

(*) Notice: Subject to any disclaimer, the term of this patent is extended or adjusted under 35 U.S.C. 154(b) by 284 days.

(21) Appl. No.: 12/810,098

(22) PCT Filed: Nov. 17, 2008

(86) PCT No.: PCT/EP2008/065628
§ 371 (c)(1),
(2), (4) Date: Jun. 22, 2010

(87) PCT Pub. No.: WO2009/095111
PCT Pub. Date: Aug. 6, 2009

(65) Prior Publication Data
US 2010/0273970 A1  Oct. 28, 2010

(30) Foreign Application Priority Data
Jan. 30, 2008  (EP) .................................. 08101089

(51) Int. Cl.
*C07C 51/16* (2006.01)
*C07C 51/42* (2006.01)
*C07C 69/52* (2006.01)
*C08F 20/06* (2006.01)

(52) U.S. Cl.
USPC ......... 562/545; 562/600; 560/205; 526/317.1

(58) Field of Classification Search .......................... None
See application file for complete search history.

(56) References Cited

U.S. PATENT DOCUMENTS 3,441,599 A   4/1969  Murayama
5,914,012 A   6/1999  Kaibel et al.
(Continued)

FOREIGN PATENT DOCUMENTS

DE  199 24 533   11/2000
DE  101 38 150    2/2003
(Continued)

OTHER PUBLICATIONS

Bai, F. et al., "Synthesis Of Monodisperse Poly (Methacrylic Acid) Microspheres By Distillation-Precipitation Polymerization", European Polymer Journal, vol. 43, No. 9, pp. 3923-3932 (Aug. 31, 2007) XP022227002.
(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for preparation of pure methacrylic acid, at least comprising the process steps: a) gas phase oxidation of a C4 compound to obtain a methacrylic acid-comprising gas phase, b) condensation of the methacrylic acid-comprising gas phase to obtain an aqueous methacrylic acid solution, c) separation of at least a part of the methacrylic acid from the aqueous methacrylic acid solution to obtain at least one crude methacrylic acid-comprising product; d) separation of at least a part of the methacrylic acid from the at least one crude methacrylic acid-comprising product by means of a thermal separation process to obtain a pure methacrylic acid.

30 Claims, 3 Drawing Sheets

U.S. PATENT DOCUMENTS

| | | | |
|---|---|---|---|
| 6,214,942 | B1 | 4/2001 | Siol et al. |
| 6,348,638 | B1 | 2/2002 | Schliephake et al. |
| 6,448,439 | B1* | 9/2002 | Eck et al. ............... 562/600 |
| 6,806,385 | B1 | 10/2004 | Hammon et al. |
| 7,109,374 | B2* | 9/2006 | Machhammer et al. ...... 562/600 |
| 2001/0016668 | A1* | 8/2001 | Mitsumoto et al. ........... 562/600 |
| 2003/0040570 | A1 | 2/2003 | Nestler et al. |
| 2004/0116741 | A1 | 6/2004 | Nordhoff et al. |
| 2004/0236049 | A1* | 11/2004 | Fuchs et al. ................. 526/317.1 |
| 2005/0222459 | A1* | 10/2005 | Nordhoff et al. ............ 562/600 |
| 2008/0119669 | A1 | 5/2008 | Balduf et al. |

FOREIGN PATENT DOCUMENTS

| | | |
|---|---|---|
| EP | 0 804 951 | 11/1997 |
| EP | 0 886 658 | 12/1998 |
| SU | 1055329 A | 11/1983 |
| WO | 02 055469 | 7/2002 |
| WO | WO 03/104300 A1 | 12/2003 |
| WO | WO 2006/084667 A1 | 8/2006 |

OTHER PUBLICATIONS

Office Action issued Oct. 18, 2012 in Russian Patent Application No. 2010135779/04(050839).

* cited by examiner

PROCESS FOR PREPARATION OF HIGH PURITY METHACRYLIC ACID

The present invention relates to a process for preparation of pure methacrylic acid, the high purity methacrylic acid obtained by this process, a device for preparation of methacrylic acid, a process for preparation of methacrylic acid esters, the methacrylic acid esters obtained by this process, a process for preparation of polymethacrylates, the polymethacrylates obtained by this process, a process for preparation of polymethacrylic acid esters, the polymethacrylic acid esters obtained by this process, the use of the pure methacrylic acid obtained by the process according to the invention and of the methacrylic acid esters obtained by the process according to the invention, as well as fibres, films, varnishes, coatings, moulding materials, formed bodies, paper additives, leather additives, flocculants and drilling additives.

Methacrylic acid ("MAA") and methacrylic acid esters, such as methyl methacrylate ("MMA") and butyl methacrylate, as well as polymeric materials comprising them, are used in a wide variety of applications. Typical end applications include acrylic plastic forms and sheets, compression-mould resins, polyvinylchloride modifiers, processing additives, acrylic varnishes, floor care products, sealing materials and sealants, automobile transmission fluids, crank case oil modification agents, motor vehicle coatings, ion exchange resins, electronics adhesives, metal coatings and acrylic fibres. MAA and methacrylic acid ester are particularly valued in these and other applications because of the hardness which they impart to the products in which they are used. They strengthen both the chemical stability and the light stability as well as the resistance to ultra-violet irradiation, when they are used in certain products. MAA and methacrylic acid ester are thus often used in applications which require resin with excellent transparency, strength and durability in outdoors applications.

Other applications are in the production of co-polymers such as the co-polymer methyl methacrylate-butadiene-styrene (MBS), which is used as a modifier for PVC; in paints and varnishes such as waterborne coatings, for example latex house paint; in adhesives; and more recently in plates that keep light spread evenly across LCD computer and TV screens, for example in flat screens, and in contact lenses. Methyl methacrylate is also used in preparation of corrosion casts of anatomical organs, such as coronary arteries of the heart.

Special methacrylate ester derivatives, for example, of alkyl and aryl alcohols, hydroxyalcohols, polyethylene glycols, quaternary ammonium derivatives and aminoalcohols, among others, have applications in, for example, contact lenses, coatings, drug delivery, controlled release of active substances, adhesives, lubricants, flow improvers, compatibility agents for polymer blends, bonding agents, food packaging, lacquers and PVC-free underseal compounds for automobile manufacture.

In many applications of methacrylic acid and/or its derivatives, the appearance, and in particular the colour of the product is of considerable significance, with products preferably being as colourless as possible.

The commercial production of methacrylic acid occurs, among other ways, by heterogeneously catalysed gas phase oxidation of isobutylene, tert-butanol, methacrolein or isobutyl aldehyde. The thus obtained, gaseous reaction phase is transformed into an aqueous methacrylic acid solution by cooling and condensing, optionally separated from low-boiling substances such as, for example, acetaldehyde, acetone, acetic acid, acrolein and methacrolein and then introduced into a solvent extraction column, in order to extract and separate methacrylic acid by means of suitable extraction agents, such as, for example, short-chain hydrocarbons. The separated methacrylic acid is further purified, for example by distillation, to separate high-boiling impurities, such as, for example, benzoic acid, maleic acid and terephthalic acid, in order to obtain a pure methacrylic acid. Such a known process is described for example in EP 0 710 643 A1. Besides this so-called $C_4$ process, methacrylic acid can also be obtained by the so-called ACH process (ACH=acetone cyanohydrin), in which hydrocyanic acid and acetone are used as starting materials. By reaction of the hydrocyanic acid with acetone, ace-tone cyanohydrin is formed, which is then converted to methacrylic acid in the presence of water and sulphuric acid. Such a process is described, for example in EP 0 999 200 A1.

In particular, the aldehydes formed as side products in the production of methacrylic acid by the $C_4$ process, which absorb in the ultra-violet range, lead, even at very low concentrations, to an undesired yellow colouration of the methacrylic acid, which also leads to an undesired colouration of the end products produced from such a methacrylic acid. The extent of colouration of the methacrylic acid is quantified by means of the so-called "APHA" number, which is often determined by the ASTM standard D 1209. Processes are thus known from the prior art, to reduce this colouration of the methacrylic acid by addition of reagents which react with such aldehydes. In this connection, for example the addition of amines is known, such as, for example, hydrazine, ethylene diamine, aniline or polyamines, or the addition of p-phenylenediamines, as described in EP 0 312 191 A2.

A disadvantage of the previous processes for production of pure methacrylic acid by the $C_4$ process is, however, that, in addition to the extraction step, at least two additional distillation steps are necessary, in order to separate the low-boiling and the high-boiling impurities. Since methacrylic acid tends, under thermal load, to form methacrylic acid dimers, methacrylic acid oligomers and methacrylic acid polymers, each additional distillation step leads to a reduction of the methacrylic acid yield by formation of dimers, oligomers or polymers.

It was thus a general object of the present invention to overcome or at least reduce the disadvantages known from the prior art.

An object of the present invention was also provide a simpler, more efficient and more time- and cost-effective means of improving purity of methacrylic acid, in particular to make it more suitable for use in its further processing products, in particular where as little colouration of the product as possible is preferred.

A contribution to the solution of at least one of the above problems is made by the subject matter of the category-forming claims. The sub-claims dependent on the category-forming claims describe preferred embodiments according to the invention.

A solution to the above objects is provided by a process for preparation of pure methacrylic acid, at least comprising the process steps:
a) gas phase oxidation of a $C_4$ compound to obtain a methacrylic acid-comprising gas phase,
b) condensation of the methacrylic acid-comprising gas phase to obtain an aqueous methacrylic acid solution,
c) separation of at least a part of the methacrylic acid from the aqueous methacrylic acid solution to obtain at least one crude methacrylic acid-comprising product;

d) separation of at least a part of the methacrylic acid from the at least one crude methacrylic acid-comprising product by means of a thermal separation process to obtain a pure methacrylic acid.

The $C_4$ compound which is subjected to gas phase oxidation in step a) of the process according to the invention is preferably a $C_4$ compound selected from isobutylene, tert-butyl alcohol and methacrolein, or a mixture of two or more thereof.

The gas phase oxidation in step a) of the process according to the invention preferably occurs in the presence of at least one oxidation catalyst. If the $C_4$ compound is isobutylene or tert-butyl alcohol, the gas phase oxidation to obtain a methacrylic acid-comprising gas phase can occur in one step, whereby one step in this context is considered to mean that initial oxidation to methacrolein and further oxidation to methacrylic acid occur substantially in the same reaction area, in the presence of at least one catalyst. Alternatively, the gas phase oxidation in step a) can occur in more than one step, preferably in two steps, preferably in two or more reaction areas separated from each other, whereby two or more catalysts are preferably present, each catalyst preferably being present in a separate reaction area from each other catalyst. In a two step gas phase oxidation, the first step is preferably at least partial oxidation of the $C_4$ compound to methacrolein, followed by at least partial oxidation of methacrolein to methacrylic acid. Accordingly, for example, in a first reaction step, preferably at least one catalyst suitable for oxidation of at least one $C_4$ compound to methacrolein is present, and in a second reaction step, at least one catalyst suitable for oxidation of methacrolein to methacrylic acid is present.

Suitable reaction conditions for gas phase catalytic oxidation are, for example, temperatures of from about 250° C. to about 450° C., preferably from about 250° C. to about 390° C. and pressures of from about 1 atm. to about 5 atm. The space velocity can vary from about 100 to about 6000 $hr^{-1}$ (NTP) and preferably from about 500 to about 3000 $hr^{-1}$. Oxidation, for example gas phase catalytic oxidation, of $C_4$ feeds such as isobutylene to methacrolein and/or methacrylic acid, as well as catalysts therefor, are well known in the literature, for example from U.S. Pat. No. 5,248,819, U.S. Pat. No. 5,231,226, U.S. Pat. No. 5,276,178, U.S. Pat. No. 6,596,901 B1, U.S. Pat. No. 4,652,673, U.S. Pat. No. 6,498,270, U.S. Pat. No. 5,198,579, U.S. Pat. No. 5,583,084.

Particularly preferred catalysts and processes suitable for oxidation of isobutylene or tert-butanol to methacrolein and/or methacrylic acid are described in EP 0 267 556 A2, and particularly preferred catalysts and processes suitable for oxidation of methacrolein to methacrylic acid are described in EP 0 376 117 A1. These documents are hereby introduced as reference and form part of the disclosure of the present invention.

The gas phase oxidation of methacrolein to methacrylic acid in the process according to the invention preferably occurs at temperatures of from about 250 to about 350° C. and below, at pressures from about 1 to about 3 atm, and at volume loads of from about 800 to about 1800 Nl/l/h.

As oxidising agent, generally oxygen is used, for example, in the form of air, or in the form of pure oxygen or oxygen diluted with at least one gas which is inert under the reaction conditions, such as at least one of nitrogen, carbon monoxide and carbon dioxide, whereby air is preferred as oxidising agent and nitrogen and/or carbon dioxide are preferred as diluent gas. If carbon dioxide is used as diluent gas, this is preferably carbon dioxide recycled from a combustion, preferably a catalytic or thermal combustion taking place after at least one of steps c), d) and e) of the process according to the invention. The gas subjected to gas phase oxidation in step a) of the process according to the invention preferably also comprises water, which is generally present in the form of water vapour. The oxygen, inert gas or gases and water can be introduced into the reaction phase or combined with the $C_4$ compound before or during or before and during the gas phase reaction.

In a preferred embodiment of the process according to the invention, a mixture comprising at least one $C_4$ compound, air or oxygen and recycled reactor exit gas, preferably reactor exit gas which has been combusted prior to recycling, is supplied to step a). The reactor exit gas preferably comprises at least one unreacted C4 compound, at least one carbon oxide, nitrogen and oxygen, as well as water, depending on the separation conditions and the presence of and action of a combustion step.

In a two-step gas phase oxidation according to the invention, a preferred volume ratio in the first step of $C_4$ compound: $O_2$:$H_2O$:inert gas is generally 1:0.5-5:1-20:3-30, preferably 1:1-3:2-10:7-20. The volume ratio in the second step of methacrolein:$O_2$:$H_2O$:inert gas is preferably 1:1-5:2-20:3-30, preferably 1:1-4:3-10:7-18.

In step b) of the process according to the invention, the gas phase which comprises methacrylic acid is condensed to obtain a condensate in the form of an aqueous methacrylic acid-comprising solution. The condensation can occur by any means known to the skilled person and appearing suitable, for example by cooling the methacrylic acid-comprising gas phase to temperatures below the dew point of at least one of its components, in particular of at least one of water and methacrylic acid. Suitable methods of cooling are known to the skilled person, for example, cooling by means of at least one heat exchanger, or by quenching, for example by spraying the gas phase with a liquid, for example with water, an aqueous composition or an organic solvent, such as, for example, aromatic or aliphatic hydrocarbons, or mixtures of at least two thereof, whereby preferred organic solvents have relatively low vapour pressure under the quenching conditions, such as heptane, toluene or xylene, whereby water is preferred according to the invention, and more preferred is at least a portion of the condensate formed in the quenching step. Suitable quenching processes are known to the skilled person, for example from DE 21 36 396, EP 297 445 A2, EP 297 788 A2, JP 01193240, JP 01242547, JP 01006233, US 2001/0007043 A1, U.S. Pat. No. 6,596,901 B1, U.S. Pat. No. 4,956,493, U.S. Pat. No. 4,618,709 B1, U.S. Pat. No. 5,248,819, whose disclosure concerning quenching of acrylic and methacrylic acids is hereby incorporated and forms part of the present disclosure. It is preferred according to the invention that the gas phase is cooled to temperatures between 40 and 80° C. and washed with water and/or condensate from the quenching step to obtain an aqueous solution comprising methacrylic acid, which can also comprise varying amounts of impurities such as acetic acid, maleic acid, fumaric acid, citraconic acid, acrylic acid and formic acid, as well as aldehydes such as formaldehyde, acetaldehyde, propionaldehyde, acrolein, methacrolein, ketones and unreacted $C_4$ compound or compounds. These impurities, as well as water, need to be separated to the greatest extent possible from the methacrylic acid in order to obtain a high degree of purity of methacrylic acid.

In a preferred embodiment of the process according to the invention, process step c) comprises process steps c1α) extraction of the methacrylic acid from the aqueous methacrylic acid solution by means of an organic extraction agent to obtain an aqueous phase and an organic phase, c1β) separation of at least a part of the organic extraction agent from the organic phase by means of at least one thermal separation process to obtain at least one methacrylic acid-comprising bottom product as crude methacrylic acid-comprising product.

The extraction of the methacrylic acid from the aqueous methacrylic acid-comprising solution occurs in process step c1α) by means of an organic extraction agent, for example at least one organic solvent, preferably at least one organic solvent which is substantially immiscible with water, such that an aqueous phase and an organic phase can be formed. Preferred organic solvents which can be used in step c) of the process according to the invention have a boiling point different to, preferably lower than, the boiling point of methacrylic acid. Preferably, in the process according to the invention, the organic extraction agent used in process step c1α) has a boiling point of less than 161° C. measured at atmospheric pressure. The organic extraction agent can then in principle be separated from methacrylic acid, for example by distillation, preferably at least partially, preferably to a substantial extent in step c1β) of the process according to the invention, where it can be at least partially removed as a low boiler at a higher level in the distillation apparatus than the pure methacrylic acid. The separated organic extraction agent can be conducted back to process step c1α), optionally after at least one cooling and/or purification step. Preferred organic solvents for this step are in particular selected from alkanes and aromatic, preferably alkylaromatic, hydrocarbons, whereby at least one organic solvent selected from heptane, toluene and xylene is particularly preferred and heptane, preferably n-heptane is most preferred. The extraction can be carried out by any means known and appearing suit-able to the skilled person, for example by means of a washing column, a phase separator or other device suitable for separation of an organic phase from an aqueous phase. At least a part, preferably at least 50 wt. %, preferably at least about 70 wt. %, preferably at least about 80 wt. %, more preferably at least about 90 wt. % of the methacrylic acid comprised in the aqueous methacrylic acid solution is extracted into the organic phase.

In step c1β) of this embodiment of the process according to the invention, the organic extraction agent is at least partially separated from the organic phase by means of a thermal separation process. Suitable thermal separation processes are known to the skilled person, whereby distillation, rectification and the like are preferred according to the invention. One or more separation processes can be carried out according to the invention. In a distillation step, components boiling at temperatures lower than methacrylic acid are removed, preferably removed at the head of a distillation column, or at appropriate levels of a fractionation column or a rectification column, and a bottom phase rich in methacrylic acid is obtained. Lower boiling components to be removed preferably overhead can be, in addition to the organic extraction agent, side products such as those mentioned above, as well as unreacted $C_4$ compound or compounds. It is further possible to at least partially recover unreacted $C_4$ compound or compounds by washing the column exit gas with water at low temperatures or by stripping it with air or inert gases. Recovered unreacted $C_4$ compound or compounds can then be conducted back to the gas phase oxidation, in order to achieve as high a conversion as possible.

In another preferred embodiment of the process according to the invention, process step c) comprises process steps
c2α) crystallisation of at least a part of the methacrylic acid from the aqueous methacrylic acid solution,
c2β) optionally, washing of the crystallised methacrylic acid,
c2g) melting of at least a part of the crystallised methacrylic acid to obtain a melted crystallised methacrylic acid as at least one crude methacrylic acid-comprising product.

The crystallisation in step c2α) can occur by methods known to the skilled person for continuous or batchwise, preferably continuous crystallisation, such as dynamic or static crystallisation or a combination of the two, for example melt crystallisation, scratch cooling crystallisation, fractional crystallisation, layer crystallisation, suspension crystallisation, falling film crystallisation and the like, or any combination of two or more thereof, whereby melt crystallisation is preferred. If a melt crystallisation is carried out in the process according to the invention, it is preferred that the crystallisation occurs in at least one crystallisation and melting cycle. In a preferred aspect of a melt crystallisation according to the invention, at least a part of the melted crystallised methacrylic acid is used to wash at least a part of the crystallised methacrylic acid. Suitable processes are described, for example, in WO 02/055469 A1, WO 99/14181 WO 01/77056 A1, U.S. Pat. No. 5,504,247, whose disclosure concerning crystallisation is hereby incorporated by reference and forms part of the present disclosure.

In step d) of the process according to the invention, the crude methacrylic acid-comprising product obtained in step c) is subjected to a further thermal separation process to separate a pure methacrylic acid. By pure methacrylic acid is meant a methacrylic acid which comprises less than 1 wt. %, preferably less than 0.8 wt. %, more preferably less than 0.5 wt. %, particularly preferably less than 0.3 wt. % impurities, based on the total weight of methacrylic acid and impurities. The thermal separation is preferably a distillation, whereby impurities with boiling points higher than methacrylic acid remain in the bottom product and pure methacrylic acid is preferably removed at a level which is higher than the bottom of the column. It is also possible to remove methacrylic acid phases at the top and/or bottom of the column. The amount of impurities comprised in the respective methacrylic acid phases determines whether they are considered to be pure methacrylic acid according to the invention.

In a preferred aspect of the process according to the invention, the at least one crude methacrylic acid-comprising product introduced into process step d) comprises at most 95 wt. %, preferably at most 90 wt. %, yet more preferably at most 85 wt. %, methacrylic acid. For example, if the organic phase obtained in process step c1α) according to the invention does not have a methacrylic acid concentration which is suitable according to this aspect of the invention, it is possible to adjust this concentration prior to the thermal separation process of step c1β) of the process according to the invention, for example by addition or removal, preferably removal, of phase components. This can be done, for example, by means of intermediate separation steps, for example distillation to remove low boilers or high boilers, filtration to remove solid impurities, crystallisation, and the like.

In a further preferred aspect of the process according to the invention, the at least one crude methacrylic acid-comprising product introduced into process step d) has been obtained by distillation or crystallisation of a composition which comprises at least 5 wt. %, preferably at least 10 wt. %, yet more preferably at least 15 wt. % of a $C_4$-$C_8$ hydrocarbon. $C_4$-$C_8$ hydrocarbons which can be comprised according to the invention are any of acetic acid, maleic acid, fumaric acid, citraconic acid, acrylic acid and formic acid, as well as aldehydes, ketones and unreacted $C_4$ compound or compounds.

In a further preferred aspect of the process according to the invention, the at least one crude methacrylic acid-comprising product introduced into process step d) has an American Public Health Association (APHA) number according to DIN ISO 6271, of at least 100, preferably at least 250 and yet more preferably at least 500. The APHA number, also referred to as the Platinum-Cobalt Colour Number or the Hazen number, provides a measurement standard for colouration of a solution or liquid with respect to a colour standard platinum-cobalt comparison solution and is typically used to characterise the yellowness of a material, whereby a higher APHA number indicates a greater degree of yellow colouration. More details concerning APHA numbers are provided in "The Measurement of Appearance", 2d ed., Richard S. Hunter and Richard W. Harold, Wiley, 1987, p. 211 and 214, and in U.S. Pat. No. 7,002,035 B2, whose disclosure is hereby introduced by reference and forms part of the disclosure of the present invention.

In a further preferred aspect of the process according to the invention, the at least one crude methacrylic acid-comprising product introduced into process step d) comprises methacrylic acid in an amount in a range from 97 wt. % to 99.7 wt. %, preferably in an amount in a range from 97.5 wt. % to 99.7 wt. %, more preferably in an amount in a range from 98.0 wt. % to 99.6 wt. %, yet more preferably in an amount in a range from 98.5 wt. % to 99.5 wt. %.

In a preferred embodiment of the process according to the invention, in process step d) the methacrylic acid is separated by means of rectification from at least a part of the at least one crude methacrylic acid-comprising product, whereby the pure methacrylic acid is removed in a side outlet from the column used for the rectification. Methacrylic acid-comprising fractions can also be removed from the head and the bottom of the rectification column.

It is preferred in this embodiment of the process according to the invention that the rectification in process step d) is carried out at a bottom pressure in a range from 0.1 to 100 mbar, preferably in a range from 0.5 to 90 mbar, more preferably in a range from 1 to 80 mbar, yet more preferably in a range from 5 to 70 mbar, more preferably in a range from 10 to 50 mbar. This pressure range, which is lower than atmospheric pressure, enables the use of lower temperatures for the rectification, making the process gentler, thereby reducing the degree of oligomerisation and polymerisation of methacrylic acid and potentially leading to increased yield with savings in energy expenditure and reduced amount of polymerisation inhibitor and/or stabiliser necessary.

It is further preferred in this aspect of the process according to the invention that the rectification in process step d) is carried out at a bottom temperature in a range from 40 to 200° C., preferably in a range from 40 to 180° C., more preferably in a range from 40 to 160° C., more preferably in a range from 50 to 140° C., yet more preferably in a range from 50 to 130° C., even more preferably in a range from 50 to 120° C., yet more preferably in a range from 50 to 110° C., even more preferably in a range from 50 to 100° C. In a particularly preferred embodiment of this aspect of the process according to the invention, the rectification in process step e) is carried out at a bottom temperature of less than 90° C.

It is further preferred in this aspect of the process according to the invention that the rectification column has more than 0 and up to 10 theoretical plates per meter, preferably from 0.5 to 8 theoretical plates per meter, more preferably from 1 to 7 theoretical plates per meter, yet more preferably from 1.5 to 6 theoretical plates per meter. A theoretical plate in distillation processes is a hypothetical zone or stage in which the liquid and vapour phases of the substance to be distilled establish an equilibrium with each other. The greater the number of theoretical plates, the greater the efficacy of the separation process. The concept, as well as the calculation, of theoretical plates is well known to the skilled person. Since actual physical plates, trays or floors, or similar means such as packed beds, for example comprising Raschig rings or other structured inserts, rarely represent a 100% efficient equilibrium stage, the number of actual plates is usually more than the required theoretical plates.

It is preferred in the process according to the invention that the liquid load factors for the rectification column lie in a range from 0.5 to 10 $m^3/m^2h$, preferably in a range from 1 to 5 $m^3/m^2h$, more preferably in a range from 1.5 to 3 $m^3/m^2h$, even more preferably in a range from 1.7 to 2.5 $m^3/m^2h$. In particular above the side outlet of the rectification column this value is substantially constant, since substantially only concentrated methacrylic acid is present in the column. The liquid load is determined according to the product properties and the selected pressure/temperature range, whereby, for example, a higher liquid load requires higher pressure and hence higher bottom temperature.

It is particularly preferred according to the invention that the pure methacrylic acid in process step d) is removed at a height in a range between the lower fourth and the upper fourth of the rectification column, preferably by means of a side outlet. This allows an improved separation from impurities boiling at higher and lower temperatures than methacrylic acid. Other methacrylic acid fractions can also be removed at different heights, as well as from the head and/or the bottom of the column. Such other methacrylic acid fractions, even if they have impurity content such that they are not considered as pure methacrylic acid according to the invention, can be generally suitable for applications or further processing reactions where a very high methacrylic acid purity is not necessary, or where separation from impurities can be carried out at a later stage without significant difficulties, for example if a desired further processing end or intermediate product has a significantly different melting or boiling point or solubility compared to any impurities present. An example of this is where further processing products are methacrylic acid esters.

In an aspect of the process according to the invention, it can be preferred that the at least one crude methacrylic acid-comprising product introduced into process step d) is subjected to a flow resistance at or after entering into the rectification column. It is possible according to the invention that the crude methacrylic acid-comprising product supplied to step d) is introduced into the rectification column at the bottom, at the head, or at any point between the bottom and the head of the rectification column. It is preferred according to the invention that the crude methacrylic acid-comprising product introduced into the rectification column is not permitted to flow directly to the side outlet or outlets for pure methacrylic acid. This is particularly preferred if the methacrylic acid-comprising bottom product is introduced by means of one or more side inlets. This can be achieved, for example, by a physical separation means such as a flow resistance upon which the crude methacrylic acid-comprising product entering the column impinges, preferably impinges in the main flow direction of the crude methacrylic acid-comprising product entering the column, preferably at an angle in the range from 60° to 120°, more preferably at an angle in the range from 70° to 110°, more preferably at an angle in the range from 80° to 100°, most preferably at an angle in the range from 85° to 95°, most preferably at an approximately perpendicular angle to the flow resistance. The angle at which the crude methacrylic acid-comprising product impinges on the flow resistance is thus preferably the angle formed by the main flow direction of the crude methacrylic acid-comprising product entering the column, with a variation of about ±30° about this main flow direction. This can be achieved by means of side inlets such as pipes, tubes, taps and nozzles, including fixed and/or pivotable inlets, known to the skilled person. If the methacrylic acid-comprising bottom product is introduced by means of a side inlet in the form of a spray nozzle, it is preferred that the opening angle of the spray nozzle is in the range of from about 60° to about 120°, preferably in the range of from about 70° to about 110°, more preferably in the range of from about 80° to about 100°, more preferably in the range of from about 85° to about 95°. The flow resistance can be, for example in the form of a separating wall, also referred to as partition, between the side inlet and the side outlet. In a preferred embodiment of the process according to the invention, the rectification column is a column comprising a flow resistance, preferably in the form of a so-called separating wall or partition, preferably a separating wall which separates at least one side inlet for methacrylic acid-comprising bottom product from at least one side outlet for pure methacrylic acid according to the invention. A separating wall of this type preferably extends at least three theoretical plates above at least one of the at least one side inlet and the at least one side outlet, preferably the higher thereof, and at least three theoretical plates below at least one of the at least one side inlet and the at least one side outlet, preferably the lower thereof.

It is also possible to prevent mixing of the incoming product with the pure methacrylic acid by arranging the side inlet at a different level compared to the side outlet, or by a combination of this arrangement with a flow resistance. If the at least one methacrylic acid-comprising bottom product obtained in process step c) is introduced into the rectification column from 1 to 5 theoretical floors below the side outlet, a separating wall may thus optionally be comprised in the rectification column. Accordingly, in another preferred aspect of the process according to the invention, the at least one crude methacrylic acid-comprising product obtained in process step c) can be introduced into the rectification column from 1 to 5 theoretical floors below the side outlet. In a further preferred aspect of the process according to the invention the at least one crude methacrylic acid-comprising product obtained in process step c) is introduced into the bottom of the rectification column.

Preferably, in the process according to the invention, the amount of pure methacrylic acid removed, preferably the amount of pure methacrylic acid removed at a side outlet of the rectification column, in a defined time interval, is 40 to 80%, preferably 50 to 80%, more preferably 60 to 80% of the amount of the amount of crude methacrylic acid-comprising product from process step c) which is introduced into the rectification column in the same time interval. The remaining amount of methacrylic acid comprised in the respective amount of crude methacrylic acid-comprising product from process step c) supplied to the rectification column in the same respective time interval is preferably withdrawn at the head and/or the bottom of the rectification column.

It is also possible in the process according to the invention that the thermal separation in process step d) is carried out in the presence of a decolourisation agent. Decolourisation agents are generally used to improve the colour of the product, at least partially by physically and/or chemically removing and/or destroying at least one coloured impurity and/or at least one precursor to a coloured impurity. Impurities which might be present in the process according to the invention comprise aldehydes and organic acids, for example formaldehyde, acetaldehyde, acrolein, methacrolein, propionaldehyde, n-butyraldehyde, benzaldehyde, furfural, crotonaldehyde, acetic acid, formic acid, propionic acid. Any decolourisation agents known to the skilled person and appearing suitable can be used according to the invention. Decolourisation agents can be, for example, materials capable of adsorbing or absorbing coloured compounds and/or precursors to coloured compounds. Examples of such materials are activated carbon, ion exchange resins, zeolites, silicates, aluminates, molecular sieves and the like, which can be in any suitable form, for example in the form of a powder, granules or pellets. Other decolourisation agents known from the prior art can also be considered, for example compounds which bind the impurities, in particular the aldehyde impurities, for example amine compounds, such as alkyl amines, aryl amines, arylalkylamines, alkanolamines, hydrazines and hydrazine derivatives. The decolourisation agent is preferably used in an amount in a range from 0 to 5 wt. %, preferably in a range from 0.0001 to 3 wt. %, more preferably in a range from 0.0005 to 3 wt. %, yet more preferably in a range from 0.005 to 2 wt. %, even more preferably in a range from 0.001 to 1 wt. %, most preferably in an amount from 0.001 to 0.5 wt. %.

If a decolourisation agent is present in the process according to the invention, it is preferred that the decolourisation agent is a hydrazine derivative, preferably an aminoguanidinium salt. In a particularly preferred embodiment of the process according to the invention, the aminoguanidinium salt is aminoguanidinium bicarbonate, also referred to as aminoguanidinium hydrogencarbonate.

If a decolourisation agent is present in the process according to the invention, the decolourisation agent is preferably added A) to the at least one crude methacrylic acid-comprising product obtained in process step c) before the thermal separation in process step d), or B) during the thermal separation in process step d).

If the decolourisation agent is added according to A) to the at least one crude methacrylic acid-comprising product obtained in process step c) before the thermal separation in process step d) of the process according to the invention, it is preferably added after the bottom product has been removed from the area in which step c) takes place and before entering into the area where step d) occurs. This addition can also take place at the same time as introducing the at least one crude methacrylic acid-comprising product obtained in process step c) into the thermal separation in process step d), for example by adding the decolourisation agent at the point of entry of the at least one crude methacrylic acid-comprising product obtained in process step c) into the thermal separation in process step d). If the decolourisation agent is added according to B) during the thermal separation in process step d), it can be added at any point appearing suitable to the skilled person, for example through an inlet at the top or bottom, or through a side inlet, of a distillation column or rectification column, preferably during operation of such a column.

In order to prevent oligomerisation and/or polymerisation, as well as other reactions of methacrylic acid during thermal processes such as those described above, it is possible to add at least one inhibitor and/or stabiliser to the process according to the invention. The addition of inhibitor and/or stabiliser can occur at any stage of the process, but preferably occurs prior to or during at least one of steps c2α) and d), or in the same way or at the same time as addition of decolourisation agent as described above. In known processes where the product is removed in vapour form at the head of the column, the product must be fully stabilised again by adding stabiliser and/or inhibitor after removal from the column, so that stabiliser must be added both to the column and to the distilled product. In the process according to the invention, addition of inhibitor and/or stabiliser can occur into the column, for example with the reflux at the head of the column during step c1β) and/or step d), preferably step d), or at a lower inlet into the column, whereby a lower inlet can be above, below, or at the same level as the side outlet for pure methacrylic acid. It is a particular advantage of the process according to the invention that the amount of stabiliser and/or inhibitor in the pure methacrylic acid drawn off through a side outlet, in particular a liquid phase side outlet, for example for drawing off methacrylic acid in liquid form, can be regulated by addition of stabiliser and/or inhibitor at the head of the column, so that a further addition of stabiliser and/or inhibitor to the pure methacrylic acid collected may not be necessary. This is possible because the liquid load is substantially equivalent throughout the column, in particular in step e) of the process according to the invention, because of the high methacrylic acid concentration prevailing throughout the column. In the process according to the invention, therefore, it may not be necessary to make a further addition of stabiliser/inhibitor to the product removed from the column. Accordingly, in a preferred aspect of the process according to the invention, stabiliser and/or inhibitor is added at the head of the column, preferably via the reflux at the head of the column. It is also possible according to the invention that an addition or a further addition of stabiliser and/or inhibitor is made to the methacrylic acid withdrawn from the column in step e) of the process according to the invention. Suitable inhibitors and stabilisers are known to the skilled person, for example hydroquinone, hydroquinone monomethyl ether, paranitrosophenol, paramethoxyphenol or phenothiazine.

In the process according to the invention, it is preferred if in process step d) less than 5 wt. %, preferably less than 1.5 wt. %, particularly preferably no impurities different from methacrylic acid are precipitated from the at least one crude methacrylic acid-comprising product obtained in process step c). Precipitation of impurities, such as polymeric and/or oligomeric methacrylates, among others, is a cause of reactor downtimes, for example for necessary cleaning and/or unblocking of the reactor, so that smaller amounts of precipitation are desired. This is the case for both discontinuous and continuous processes, but in particular for continuous processes.

In a preferred aspect of the process according to the invention, at least process step d) is carried out continuously. While a discontinuous, for example batchwise, operation is not excluded according to the invention, a continuous operation is preferred. Continuous in this context means that the at least one crude methacrylic acid-comprising product obtained in process step c) is continuously supplied to process step d) and pure methacrylic acid, as well as optionally other methacrylic acid phases, is continuously removed in process step d).

The invention also relates to a device for preparation of methacrylic acid, comprising at least the following components in fluid-conducting communication with each other:
a1) a gas phase oxidation unit;
b1) an absorption unit;
c1) a separation unit; and
d1) a purification unit;
wherein the purification unit comprises at least one distillation column, the at least one distillation column comprising at least one side outlet for pure methacrylic acid.

The term "in fluid-conducting communication" is understood here as meaning that the units are connected such that a fluid, which can be at least one of a liquid, a gas, a vapour, a supercritical fluid or any other fluid, can be conducted from one unit to at least one other unit. This can be achieved, for example by direct communication via tubes or pipes, for example made of a material which is resistant to the reagents and conditions prevailing, such as stainless steel or glass, or any other suitable material known to the skilled person, or indirectly by means of tank vehicles or a tank or reservoir arranged between units. If a gas is to be conducted and should remain in gaseous form, the means of conducting the gas is preferably maintained at a temperature above the dew point of the gas. If a liquid is to be conducted, the means of conducting the liquid is preferably maintained at a temperature above the solidification and/or precipitation point of the liquid and/or components present in the liquid. This can be achieved by means of insulating and/or heating the means of conducting the respective gas or liquid. All reactors, columns, and other device components are preferably made from a material which is resistant to the reagents and conditions, such as temperature and pressure conditions in particular, to which they are subjected.

The gas phase oxidation unit preferably comprises at least one reactor suitable for carrying out a gas phase reaction, in particular a pressure reactor, preferably at least one multitube reactor, formed for example as a tube and shell reactor, and/or at least one plate reactor and/or at least one fluidised bed reactor, whereby a multitube reactor is preferred. Particularly preferred is at least one multitube reactor in which oxidation catalyst is arranged in at least one tube, preferably wherein the tubes are packed or coated, preferably packed, with oxidation catalyst. Oxidation catalysts preferred according to the invention are those mentioned above in connection with the inventive process. The reactor materials should be resistant and preferably inert to the reagents and prevailing conditions inside the reactor. Suitable reactors are commercially available, for example from MAN DWE GmbH, Deggendorfer Werft, Germany, or from IHI Corporation, Japan, and form part of the general knowledge of the person skilled in the art.

In a two stage gas phase oxidation, the gas phase oxidation unit can comprise at least two reaction zones, each comprising oxidation catalyst. The at least two reaction zones can be at least two reaction zones in a single reactor, or at least two reactors. The oxidation catalyst in a first reaction zone is preferably an oxidation catalyst for oxidation of at least one $C_4$ compound, preferably isobutylene and/or tert-butanol, to methacrolein, and the oxidation catalyst in a second reaction zone is preferably suitable for oxidation of methacrolein to methacrylic acid. Suitable catalysts are mentioned above in connection with the process according to the invention.

In a preferred aspect of the apparatus of the present invention, at least one supply for at least one source of oxidant, preferably oxygen, preferably air, and at least one supply for water and/or steam, are in fluid communication with the gas phase oxidation unit. If the gas phase oxidation unit comprises at least a first and a further oxidation area, the apparatus can comprise, for each oxidation area, at least one supply for at least one oxidant source and at least one supply for water and/or steam. The apparatus can further comprise a supply for a diluent such as nitrogen, argon and/or carbon dioxide, preferably nitrogen or carbon dioxide, for example carbon dioxide-comprising recycle gas from a catalytic combustion unit (CCU) or a thermal combustion unit (TCU). The respective supplies should be made of a material which is resistant to the reagents and conditions prevailing, for example, stainless steel or glass. In a preferred design the oxygen, diluent and water are supplied to the $C_4$ flow before entry into the respective reactor, so that a preformed mixture enters the reactor.

In a preferred embodiment of the apparatus according to the invention, the absorption unit is a quench unit. It is preferred that methacrylic acid present in the oxidation phase leaving the catalytic reaction zone is condensed in the absorption unit to form a solution, preferably an aqueous solution, comprising methacrylic acid as main oxidation product. Unreacted methacrolein can also be separated in the absorption unit and, if desired, conducted back to the gas phase oxidation zone for further reaction. Absorption units suitable for use in the apparatus according to the invention are known to the skilled person. Step b) of the process according to the invention is preferably carried out in the absorption unit.

In a preferred embodiment of the device according to the invention, the separation unit comprises
C1a) an extraction unit, and
C2a) at least one first distillation column,
wherein the at least one first distillation column comprises at least one lower outlet in fluid-conducting communication with the at least one distillation column.

In this embodiment of the device according to the invention, the absorption unit is followed by an extraction unit. The methacrylic acid-comprising aqueous solution formed in the absorption unit is conducted to the extraction unit, where an organic solvent is provided, into which solvent methacrylic acid is preferably substantially extracted. The organic solvent is preferably substantially immiscible with water, so that an aqueous phase which is at least partially depleted in methacrylic acid, and a methacrylic acid-comprising organic phase are formed. Details regarding preferred organic solvents are given above in the description of process step c1α).

The at least one first distillation column of the separation unit according to the invention is preferably designed to correspond with process step c1β) of the process according to the invention. The first distillation column of the separation unit and the at least one distillation column of the purification unit can be connected with each other directly, such that the methacrylic acid-comprising bottom product from the first distillation column of the separation unit is conducted directly to the distillation column of the purification unit. It is also possible that at least one further component is arranged before, between or after one or both of these distillation columns. Such further components can be selected from any known to the skilled person and appearing suitable, such as at least one absorber, crystalliser, extractor, filter, heating, cooling and/or wash device. In a preferred embodiment of the device according to the invention, the bottom of the first distillation column of the separation unit is connected via a line to an inlet at the at least one distillation column of the purification unit. The inlet at the at least one distillation column of the purification unit can be a side inlet, a head inlet, for example into the reflux of the head products after condensation, or a bottom inlet.

In another preferred embodiment of the device according to the invention, the separation unit comprises
C1b) a crystallisation unit, and
C1c) optionally, a wash unit.

According to this embodiment of the device according to the invention, the absorption unit is followed by a crystallisation unit and optionally a wash unit. In the crystallisation unit, the aqueous methacrylic acid solution obtained in the absorption unit is generally cooled so that methacrylic acid at least partially crystallises out. The resulting slurry may then be pumped to a wash unit, for example a wash column, where the solid crystals are at least partially separated and washed to at least partially remove impurities. At least a part of the optionally washed crystals is melted and at least a part of the melted part either passed to the next device component or used as wash liquid, or both. It is also possible that at least a part of the crystals is supplied to the crystallisation unit as crystallisation seed. A melting device may also be comprised in the separation unit. The melting device may be internal or external to at least one of the crystallisation unit and the wash unit. The crystallisation unit can be any crystallisation unit known to the skilled person and appearing suitable for crystallisation of methacrylic acid from a crude methacrylic acid aqueous solution. Suitable crystallisation units are those commercially available from Sulzer Chemtech AG, Switzerland or Niro Process Technology B.V., The Netherlands. Examples of suitable crystallisation units, wash units and melting units are given in the literature cited in connection with process step c2α).

It is possible for the device according to the invention to further comprise additional components between the absorption unit and the extraction unit or the crystallisation unit, for example a distillation column, preferably a distillation column for at least partially separating low-boilers, a filter for separation of insoluble impurities and/or side products comprised in the product exiting the absorption unit and/or a cooling and/or heating unit. In a preferred design a distillation column for low boilers and optionally also a filter are arranged downstream of the quench unit and upstream of the extraction unit.

In a particularly preferred embodiment of the device according to the invention, the at least one distillation column of the purification unit comprises a side outlet for removal of pure methacrylic acid. The height of the side outlet, that is, the position of the side outlet between the top and bottom of the column, should be selected based on the length of the column and the desired purity and composition of the pure methacrylic acid, as well as the amounts and types of impurities comprised in the feed to the column. The closer the side outlet is to the top of the column, the more low-boiling impurities may be comprised in the pure methacrylic acid. The closer the side outlet is to the bottom of the column, the more high-boiling impurities may be comprised in the pure methacrylic acid. Pure methacrylic acid according to the invention may still comprise small amounts of impurities, as described above in connection with the process according to the invention. The at least one distillation column of the purification unit can also comprise a head outlet and/or a bottom outlet for respective methacrylic acid phases. These methacrylic acid phases are considered to be pure methacrylic acid according to the invention if they comprise the above-defined small amounts of impurities. These methacrylic acid phases, particularly if they comprise greater amounts of impurities than the pure methacrylic acid according to the invention, can be used in preparation of further processing products, in particular in the preparation of methacrylic acid esters.

Unreacted methacrolein can be separated in any of the absorption unit, the extraction unit, the at least one first distillation column of the separation unit, the crystallisation unit, the purification unit, or any of the above-mentioned further device components, and, if desired, conducted back to the gas phase oxidation unit for further reaction.

In a preferred embodiment of the device according to the invention, at least one distillation column in the purification unit is a rectification column. Preferred rectification columns comprise more than 0 and up to 10 theoretical plates per meter, preferably from 0.5 to 8 theoretical plates per meter, more preferably from 1 to 7 theoretical plates per meter, yet more preferably from 1.5 to 6 theoretical plates per meter. Since actual physical plates, trays or floors, for example bubble-cap trays, or similar means such as packed beds, for example comprising Raschig rings or other structured inserts, rarely represent a 100% efficient equilibrium stage, the number of actual plates is usually more than the required theoretical plates. The number of actual plates depends on the type of plates used and can be calculated by the skilled person or determined by means of simple experiments, for example using the comparative system chlorobenzene/ethylbenzene according to Chemie-Ingenieur-Technik, Vol. 59, Issue 8, p. 652-653.

The crude methacrylic acid-comprising product from the separation unit can be introduced into the at least one distillation column of the purification unit by means of a head inlet, a bottom inlet or a side inlet. In a preferred embodiment of the device according to the invention, the rectification column comprises at least one side inlet for the at least one crude methacrylic acid-comprising product. The side inlet can be in any form suitable for introducing the crude methacrylic acid-comprising product into the column, such as one or more pipes, tubes, taps and nozzles, which may be fixed and/or pivotable. The height of the side inlet can be selected depending on various factors, such as the height of the side outlet for pure methacrylic acid, and the temperature and/or composition of the crude methacrylic acid-comprising product at entry into the distillation column of the purification unit.

In a further preferred embodiment of the device according to the invention, the rectification column is a column comprising a flow resistance, preferably in the form of a so-called separating wall (partition). This embodiment is particularly preferred if the crude methacrylic acid-comprising product is introduced into the rectification column by means of one or more side inlets, preferably in order to separate this or these side inlets from the side outlet or outlets and prevent mixing of the product entering the column with pure methacrylic acid exiting the column. It is preferred according to the invention that the partition acts as a flow resistance upon which the crude methacrylic acid-comprising product entering the column impinges, preferably impinges in the main flow direction of the crude methacrylic acid-comprising product entering the column, preferably at an angle in the range of from 60° to 120°, preferably at an angle in the range of from 70° to 110°, more preferably at an angle in the range of from 80° to 100°, most preferably at an angle in the range of from 85° to 95°, most preferably at an approximately perpendicular angle to the flow resistance. If the side inlet is in the form of a spray nozzle, the opening angle of the spray nozzle is preferably in the range of from about 60° to about 120°, preferably in the range of from about 70° to about 110°, more preferably in the range of from about 80° to about 100°, more preferably in the range of from about 85° to about 95°. By a separating wall column is understood a column comprising a wall or plate extending in a longitudinal axis of the column such that the column is at least partially, but not completely, separated into two sections along its longitudinal axis. The separating wall may extend to and be held in place by the walls, the top and/or the bottom of the column, whereby the separating wall is preferably not attached to the column along its entire length. Separating wall columns, also referred to as partitioned columns, are known to the person skilled in the art and are commercially available. The length of the separating wall is preferably such that it extends at least three theoretical separation stages above and below at least one of a side inlet (feed) for introducing crude methacrylic acid-comprising product into the column, and a side outlet for pure methacrylic acid. In particular, the separating wall preferably extends at least three theoretical plates above at least one of the at least one side inlet and the at least one side outlet, preferably the higher thereof, and preferably at least three theoretical plates below at least one of the at least one side inlet and the at least one side outlet, preferably the lower thereof. If the at least one crude methacrylic acid-comprising product is introduced into the rectification column from 1 to 5 or more theoretical floors below the side outlet, it is not always preferred that a separating wall is comprised in the rectification column.

The invention also relates to a process according to the invention, wherein the process takes place in a device according to the invention.

The invention also relates to pure methacrylic acid obtainable by a process according to the invention.

While step d) of the process according to the invention, and the apparatus details concerning the final purification stage component d) of the device according to the invention, refer in the above description to methacrylic acid obtained by gas phase catalytic oxidation of a $C_4$ starting compound, this step and component respectively are also suitable for purification of methacrylic acid obtained by other processes, such as the ACH (acetone cyanohydrin) process, as well as for purification of acrylic acid, in particular acrylic acid obtained by gas phase oxidation of a $C_3$ compound such as propylene and/or acrolein.

The invention also relates to a process for preparation of methacrylic acid esters, comprising the process steps A) preparation of pure methacrylic acid by a process according to the invention, and
B) esterification of the pure methacrylic acid.

Methacrylate esters according to the invention preferably have formula $[CH_2=C(CH_3)C(=O)O]_n$—R, and can be formed by esterification of methacrylic acid with an alcohol of formula $R(OH)_m$, whereby n and m represent an integer from 1 to 10, preferably from 1 to 6, more preferably from 1 to 5, more preferably from 1 to 4, more preferably from 1 to 3 and R is selected from the group consisting of linear or branched, saturated or unsaturated, aliphatic or aromatic, ring or straight chain hydrocarbons and linear or branched, saturated or unsaturated, aliphatic or aromatic, ring or straight chain hetero-atom-comprising hydrocarbons, for example alkyls, hydroxyalkyls, aminoalkyls, other nitrogen- and/or oxygen-comprising residues, glycols, diols, triols, bisphenols, fatty acid residues, whereby R preferably represents methyl, ethyl, propyl, iso-propyl, butyl, in particular n-butyl, iso-butyl, hydroxyethyl, preferably 2-hydroxyethyl, and hydroxypropyl, preferably 2-hydroxypropyl or 3-hydroxypropyl, 2-ethylhexyl, isodecyl, cyclohexyl, isobornyl, benzyl, 3,3,5-trimethyl cyclohexyl, stearyl, dimethylaminoethyl, dimethylaminopropyl, 2-tert-butyl aminoethyl, ethyl triglycol, tetrahydrofurfuryl, butyl diglycol, methoxypoly-ethylene glycol-350, methoxypolyethylene glycol 500, methoxypolyethylene glycol 750, methoxypolyethylene glycol 1000, methoxypolyethylene glycol 2000, methoxypolyethylene glycol 5000, allyl, ethylene glycol, diethylene glycol, triethylene glycol, polyethylene glycol 200, polyethylene glycol 400, 1,3-butanediol, 1,4-butanediol, 1,6-hexanediol, glycerol, diurethane, ethoxylated bisphenol A, ethoxylated bisphenol A with 10 ethylene oxide units; trimethylolpropane, an ethoxylated $C_{16}$-$C_{18}$ fatty alcohol such as, for example, with 25 ethylene oxide units, 2-trimethylammonium ethyl.

The methacrylic acid esters can also be prepared from methyl methacrylate by other methods known to the skilled person, for example by transesterification. In a further possible preparation of the hydroxyester derivatives, methacrylic acid according to the invention is reacted in a ring-opening reaction with a corresponding oxygen-comprising ring, for example an epoxide, in particular ethylene oxide or propylene oxide.

The invention also relates to methacrylic acid esters obtainable by a process according to the invention. The methacrylate esters preferably have formula $[CH_2=C(CH_3)C(=O)O]_n$—R, wherein n and R are as defined above. Preferred methacrylate esters are alkyl methacrylates, in particular methyl, ethyl, propyl, iso-propyl, butyl, methacrylates, in particular n-butyl, iso-butyl, sec-butyl methacrylates, in particular n-butyl methacrylate, isobutyl methacrylate, hydroxyester methacrylate derivatives, for example hydroxyethyl methacrylate, preferably 2-hydroxyethyl methacrylate, and hydroxypropyl methacrylate, preferably 2-hydroxypropyl methacrylate or 3-hydroxypropyl methacrylate, and special methacrylate esters ethyl methacrylate, 2-ethylhexyl methacrylate, isodecyl methacrylate, cyclohexyl methacrylate, isobornyl methacrylate, benzyl methacrylate, 3,3,5-trimethyl cyclohexyl methacrylate, stearyl methacrylate, dimethylaminoethyl methacrylate, dimethylaminopropyl methacrylate, 2-tert-butyl aminoethyl methacrylate, ethyl triglycol methacrylate, tetrahydrofurfuryl methacrylate, butyl diglycol methacrylate, methoxypolyethylene glycol-350 methacrylate, methoxypoly-ethylene glycol 500 methacrylate, methoxypolyethylene glycol 750 methacrylate, methoxypolyethylene glycol 1000 methacrylate, methoxypolyethylene glycol 2000 methacrylate, methoxypolyethylene glycol 5000 methacrylate, allyl methacrylate, a methacrylic ester of an ethoxylated (optionally, for example, with 25 mol EO) $C_{16}$-$C_{18}$ fatty alcohol, 2-trimethylammonium ethyl methacrylate chloride; ethylene glycol dimethacrylate, diethylene glycol dimethacrylate, triethylene glycol dimethacrylate, polyethylene glycol 200 dimethacrylate, polyethylene glycol 400 dimethacrylate, 1,3-butanediol dimethacrylate, 1,4-butanediol dimethacrylate, 1,6-hexanediol dimethacrylate, glycerol dimethacrylate, diurethane dimethacrylate, ethoxylated bisphenol A dimethacrylate, ethoxylated (optionally, for example, with 10 EO) bisphenol A dimethacrylate; trimethylolpropane trimethacrylate, whereby methyl methacrylate, butyl methacrylates and hydroxyester methacrylate derivatives are particularly preferred.

The invention also relates to a process for preparation of polymethacrylates, comprising the process steps
i) preparation of pure methacrylic acid by a process according to the invention, and
ii) radical polymerisation of the pure methacrylic acid, optionally in the presence of monomers which are co-polymerisable with methacrylic acid.

The polymerisation is not particularly limited and can be carried out by any method known to the skilled person and appearing suitable, for example as described in U.S. Pat. No. 5,292,797, U.S. Pat. No. 4,562,234, U.S. Pat. No. 5,773,505, U.S. Pat. No. 5,612,417, U.S. Pat. No. 4,952,455, U.S. Pat. No. 4,948,668, U.S. Pat. No. 4,239,671. Preferred polymerisation methods are radical polymerisation, initiated by initiators which decompose into radicals under the polymerisation conditions, whereby the polymerisation is preferably a solution or an emulsion polymerisation, preferably an aqueous solution polymerisation.

Examples of co-monomers which can be co-polymerised with methacrylic acid are acrylamides and methacrylamides, acrylic acid esters and other methacrylic acid esters, such as methyl acrylate, ethyl acrylate, propyl acrylate or butyl acrylate, ethyl methacrylate, propyl methacrylate or butyl methacrylate, as well as acetates such as vinyl acetate, styrene, butadiene and acrylonitrile. The at least one co-monomer is most preferably at least one co-monomer selected from the group consisting of: styrene, butadiene, acrylonitrile, butyl acrylate, vinyl acetate, methyl acrylate.

The polymerisation can also take place in the presence of one or more crosslinkers. Preferred cross-linkers according to the invention are compounds which have at least two ethylenically unsaturated groups in one molecule, compounds which have at least two functional groups which can react with functional groups of the monomers in a condensation reaction, in an addition reaction or a ring-opening reaction, compounds which have at least one ethylenically unsaturated group and at least one functional group which can react with functional groups of the monomers in a condensation reaction, an addition reaction or a ring-opening reaction, or polyvalent metal cations.

The invention also relates to polymethacrylate obtainable by a process according to the invention.

The invention also relates to a process for preparation of polymethacrylic acid esters, comprising the process steps
i) preparation of methacrylic acid esters by a process according to the invention, and
ii) radical polymerisation of the methacrylic acid esters, optionally in the presence of monomers which are co-polymerisable with methacrylic acid esters.

The above details concerning polymerisation of methacrylic acid also apply to the polymerisation of methacrylic acid esters according to the invention.

The invention also relates to polymethacrylic acid esters obtainable by a process according to the invention.

The invention also relates to use of a pure methacrylic acid obtainable by a process according to the invention or of a methacrylic acid ester obtainable by a process according to the invention in fibres, films, varnishes, coatings, moulding materials, formed bodies, paper additives, leather additives, flocculants, water-soluble polymers, methacrylic anhydride and drilling additives.

The invention also relates to fibres, films, varnishes, coatings, moulding materials, formed bodies, paper additives, leather additives, flocculants, water-soluble polymers, methacrylic anhydride and drilling additives, which are based on a pure methacrylic acid obtained by a process according to the invention or on a methacrylic acid ester obtained by a process according to the invention.

The invention is more closely illustrated by the following non-limiting figures and examples.

FIGURES

Figure 3:
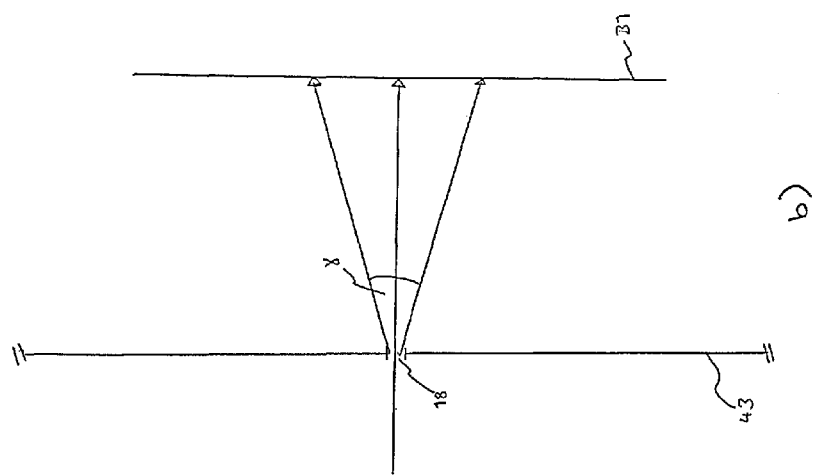
Figure 3:
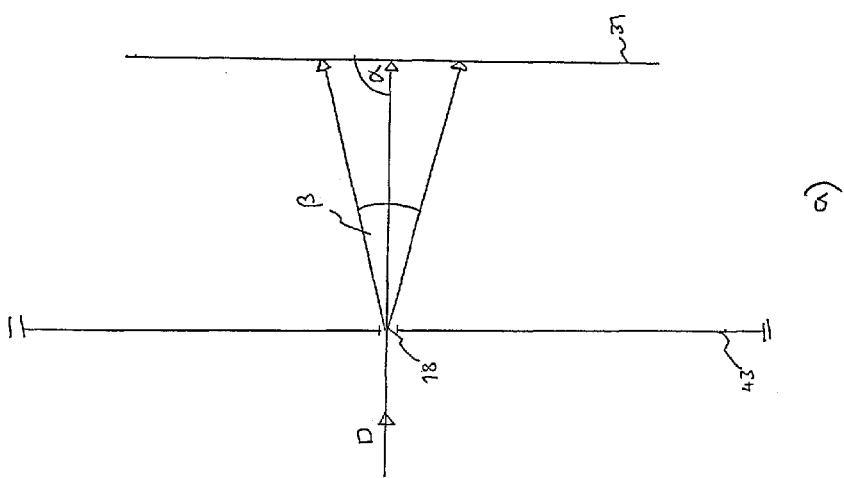

FIG. 3 a) and b) illustrate schematically angles with which a crude methacrylic acid-comprising phase impinges on a separating wall of a rectification column with a separating wall.

Figure 1:
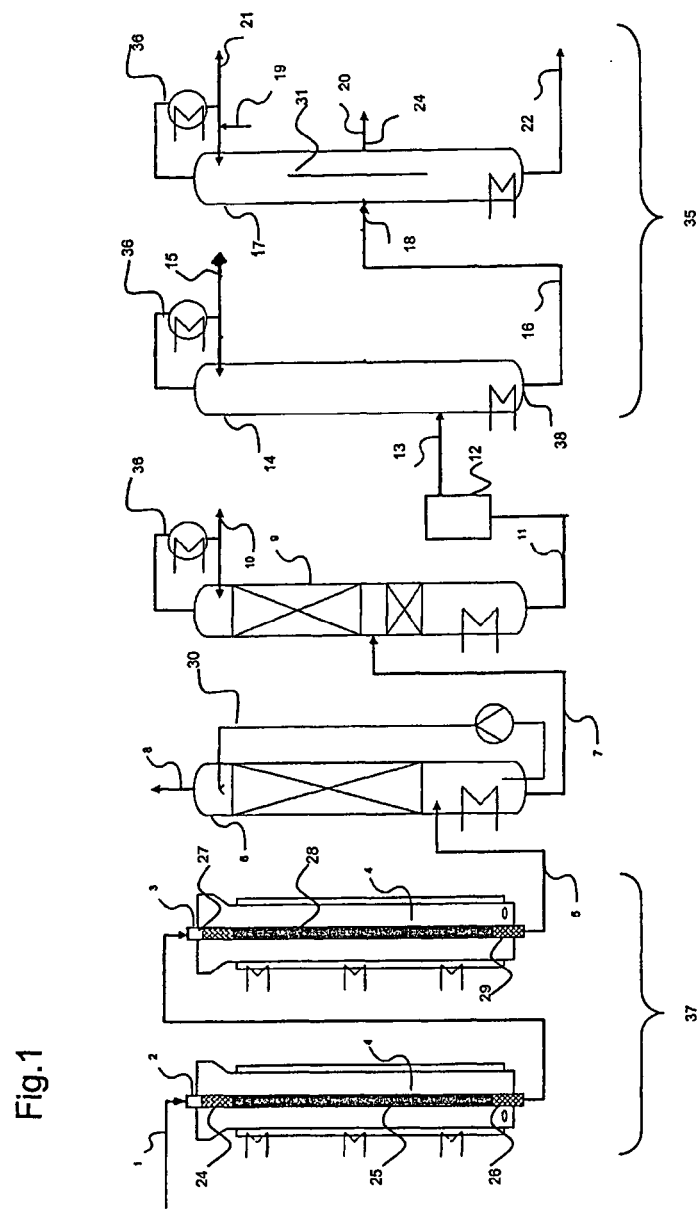
FIG. 1 shows a schematic representation of a device for preparation of methacrylic acid via two stage gas phase oxidation, with a separation unit shown as comprising an extraction unit and a first distillation column, wherein the distillation column of the purification unit is designed as a rectification column with a separating wall and with a side outlet for pure methacrylic acid.

According to FIG. 1, a $C_4$ compound such as isobutylene and/or tert-butanol, together with air and steam, flow 1, is introduced into a first reaction tube 2 with a diameter of 25 mm and a length of 2 m, heatable by means of a salt bath 4. In reaction tube 2 it passes first through an inert zone 24, then over a first oxidation catalyst 25, where it is at least partially oxidised to methacrolein, to form a first oxidation phase, and then through another inert zone 26. The first oxidation phase is then conducted to a second reaction tube 3 of similar construction to reaction tube 2, where it passes through an inert zone 27, then over a second oxidation catalyst 28, where the methacrolein is at least partially oxidised to methacrylic acid, and then through another inert zone 29, to form a second, methacrylic acid-comprising oxidation phase 5. This crude methacrylic acid gaseous phase 5 then passes to quench tower 6 where it is condensed to form an aqueous crude methacrylic acid solution 7. Some low boilers, preferably including methacrolein and/or unreacted $C_4$ compound, can be removed via an outlet 8 at the head of the column. Quench agent can be recycled and re-used in the quench column via conduit 30. The aqueous methacrylic acid phase 7 is then conducted to a low boilers distillation column 9 where low boilers 10 such as acetone and methacrolein are removed overhead. The resulting aqueous methacrylic acid solution 11 is withdrawn from the bottom of column 9 and the methacrylic acid extracted into an organic phase in extraction unit 12. The resulting methacrylic acid organic phase 13 is then conducted to a distillation column 14 (corresponding to the first distillation column of the separation unit 39 according to the invention; although a side inlet is shown for column 14, organic phase 13 can also enter at the head or at the bottom of the column 14) where it is separated from low boilers 15. The crude methacrylic acid-comprising product 16 is then conducted to column 17, where it enters via inlet 18. Inlet 18 is shown as a side inlet, but a bottom inlet is also possible. Column 17 comprises separation-effective plates (not shown) and has a separating wall 31 arranged along the longitudinal axis of the column 17. In operation, a methacrylic acid stream 14 enters into the column 17 at the side of the column, such that at least a part of the methacrylic acid stream 14 impinges on the separating wall 31. Inhibitor and/or stabiliser can be added at the top of the column 17 via stabiliser supply 19. A pure methacrylic acid phase 20 is withdrawn at side outlet 24. Inlet 18 and outlet 24 represent a schematic way of describing a separation of the column into different zones. The separating wall 31 should usually extend over at least three theoretical plates on either side (above and below) of at least one of the inlet 18 and the outlet 24. Further methacrylic acid phases 21, 22 are withdrawn respectively at the top and at the bottom of column 17. These further methacrylic acid fractions 21, 22 can be used as feed for further processing reactions such as for the esterification to form methyl methacrylate (not shown). Distillation columns 9, 14 and 17 preferably have a reflux cycle 36 overhead for reflux of low boilers for the respective column. Although the separation unit 39 is shown in the form of extraction unit 12 and distillation column 14, it is equally possible that the separation unit 39 is present in the form of a crystallisation unit 40 and optionally a wash column 41, as well as optionally a melter 42, if an external melter is used.

Figure 2:
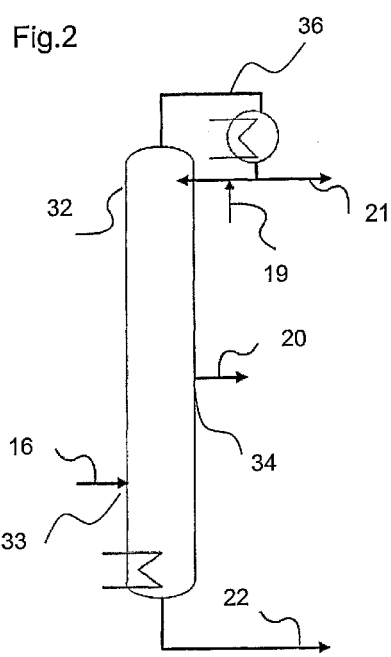
FIG. 2 shows a schematic illustration of another embodiment of a second distillation column for the purification unit, which is designed as a rectification column without a separating wall, with a side inlet below the side outlet for pure methacrylic acid.

The alternative embodiment of the rectification column for the purification unit according to the invention, column 32 as illustrated in FIG. 2, does not have a separating wall. In other respects, the description of column 17 of FIG. 1 also applies to column 32 of FIG. 2. Inlet 33 for crude methacrylic acid-comprising product 16 is shown as a side inlet, but a bottom inlet is also possible. In this embodiment without a separating wall, inlet 33 is at least one theoretical plate lower than outlet 34 for pure methacrylic acid 20, usually from one to five theoretical plates lower, or it is a bottom inlet.

FIG. 3 a) shows the preferred angles at which the crude methacrylic acid-comprising product impinges on the separating wall 31 of a column. The crude methacrylic acid-comprising product entering the column impinges on the separating wall 31 with an impinge angle α. The angle α is preferably described by the main flow direction D at the separating wall 31 of the crude methacrylic acid-comprising product entering the column, and is preferably an angle in the range of from 60° to 120°, preferably an angle in the range of from 70° to 110°, more preferably an angle in the range of from 80° to 100°, most preferably an angle in the range of from 85° to 95°, most preferably approximately perpendicular to the separating wall. The angle at which the crude methacrylic acid-comprising product impinges on the separating wall 31 in this figure is thus the angle formed by the main flow direction D with respect to the separating wall 31, with a variation β of about ±30° about this main flow direction D. If the side inlet 18 is in the form of a spray nozzle, as shown schematically in FIG. 3 b), the opening angle γ of the spray nozzle is preferably in the range of from about 60° to about 120°, preferably in the range of from about 70° to about 110°, more preferably in the range of from about 80° to about 100°, more preferably in the range of from about 85° to about 95°.

EXAMPLES

Test Methods

The Pt—Co APHA number was determined photometrically according to the method described in U.S. Pat. No. 7,002,035 B2.

Oxidation Catalysts

Oxidation catalyst I (first oxidation catalyst) was prepared according to Example 1 of EP 0 267 556 A2. Oxidation catalyst II (second oxidation catalyst) was pre-pared according to Example 1 of EP 0 376 117 A1.

Example 1

A device according to FIG. 1 was used, with the difference that instead of column 17, a column according to FIG. 2 (column 32) was used as distillation column of the purification unit. The salt bath temperatures of the first and second reaction tubes were respectively 360° C. for the first reactor and 300° C. for the second reactor. Isobutylene (5 vol. %) was oxidised in two steps with air (85 vol. %) and water (10 vol. %) to form a gaseous, methacrylic acid-comprising reaction product. This reaction product was condensed in a quench column to form an aqueous methacrylic acid solution and then separated from low boiling components in a first distillation column. An aqueous methacrylic acid solution was obtained with composition of non-methacrylic acid components as given in Table 1 (whereby the total weight including methacrylic acid adds up to 100 wt. %). The methacrylic acid was extracted from the aqueous methacrylic acid solution with n-heptane as described in EP 0 710643 A1. The resulting methacrylic acid-comprising n-heptane solution had a composition of non-methacrylic acid components according to Table 1 (whereby the total weight including methacrylic acid adds up to 100 wt. %). This solution was then subjected to distillation to remove low boilers and obtain a methacrylic acid-comprising bottom product (crude methacrylic acid) with a composition of non-methacrylic acid components as given in Table 1 under crude methacrylic acid (whereby the total weight including methacrylic acid adds up to 100 wt. %). This crude methacrylic acid bottom product was then continuously supplied to a distillation column with separation-effective inserts (4 plates per meter). This column was operated at a bottom temperature of 78° C. and a head pressure of 24 mbar. In order to prevent undesired polymerisation, a hydroquinone-based polymerisation inhibitor was introduced in the reflux of the column. At the top and bottom of the column are withdrawn methacrylic acid-rich streams, which can be used for esterification of the methacrylic acid comprised therein with alcohols. A pure methacrylic acid with composition of impurities according to Table 1 (the amount of methacrylic acid making the total weight including methacrylic acid up to 100 wt. %) was withdrawn at a side outlet.

TABLE 1

| Components | Aqueous methacrylic acid | n-Heptane extract | Crude methacrylic acid | Pure methacrylic acid |
|---|---|---|---|---|
| Water | 53 wt. % | 1500 ppm | 170 ppm | 80 ppm |
| n-Heptane | — | 79 wt. % | — | — |
| Propionic acid | 0.1 wt. % | 0.08 wt. % | 120 ppm | 35 ppm |
| Acrylic acid | 0.5 wt. % | 0.3 wt. % | 420 ppm | 105 ppm |
| Furfural | 10 ppm | 30 ppm | 70 ppm | <5 ppm |
| Benzaldehyde | 1800 ppm | 800 ppm | 1300 ppm | <5 ppm |
| Sum carbonyl comp. | 1.2 wt.-% | 1000 ppm | 1600 ppm | <10 ppm |
| High boilers | 5 wt. % | 0.15 wt. % | 0.4 wt. % | <10 ppm |
| Non-volatile comp. | 1 wt. % | 800 ppm | 0.1 wt. % | — |
| APHA (Pt—Co) | >1000 | >800 | >500 | 4 |

Comparative Example 1a

The details of this example correspond to those of Example 1, except that methacrylic acid with composition according to Table 2 was withdrawn at the head of the rectification column with separation-effective inserts.

Example 2

A device according to FIG. 1 was used, with crude methacrylic acid side inlet and pure methacrylic acid side outlet at similar heights in the rectification column. Methacrylic acid with composition according to Table 2 was withdrawn continuously at the pure methacrylic acid side outlet.

Example 3

This example corresponds to Example 1, whereby aminoguanidine bicarbonate (1000 ppm) was added into the reflux of the rectification column. Methacrylic acid with composition according to Table 2 was withdrawn continuously at the head of the column.

Example 4

This example corresponds to Example 1, whereby a holding container for crude methacrylic acid was introduced before the rectification column and aminoguanidine bicarbonate (1000 ppm) was added into the holding container (treatment at 50° C. with 1 h residence in the holding container). The mixture from the holding container was then introduced into the rectification column and distilled as above. Methacrylic acid with composition according to Table 2 was withdrawn continuously at the side outlet of the column.

Comparative Example 4a

This example corresponds to Example 4, whereby methacrylic acid was withdrawn at the top of the column and not at the side.

TABLE 2

|  | Example 1 | Example 1a | Example 2 | Example 3 | Example 4 | Example 4a |
|---|---|---|---|---|---|---|
| Methacrylic acid | 99.91 wt. % | 99.78 wt. % | 99.95 wt. % | 99.93 wt. % | 99.95 wt. % | 99.88 wt. % |
| Water | 80 ppm | 350 ppm | 60 ppm | 290 ppm | 70 ppm | 300 ppm |
| Propionic acid | 35 ppm | 150 ppm | 30 ppm | 170 ppm | 40 ppm | 180 ppm |
| Acrylic acid | 105 ppm | 450 ppm | 90 ppm | 520 ppm | 100 ppm | 520 ppm |
| Furfural | <5 ppm | 8 ppm | <5 ppm | <5 ppm | <5 ppm | <5 ppm |
| Benzaldehyde | <5 ppm | <5 ppm | <5 ppm | <5 ppm | <5 ppm | <5 ppm |
| Sum carbonyl comp. | <10 ppm | <10 ppm | <10 ppm | <10 ppm | <10 ppm | <10 ppm |
| High boilers | <10 ppm | <10 ppm | <10 ppm | <10 ppm | <10 ppm | <10 ppm |
| Non-volatile comp. | — | — | — | — | — | — |
| APHA (Pt—Co) | 4 | 8 | <3 | 3 | <3 | 4 |

Example 5

Preparation of Hydroxyesters of Pure Methacrylic Acid

Following the procedure according to U.S. Pat. No. 3,875,211, 60 parts by weight of methacrylic acid, 0.16 parts by weight of hydroquinone monomethyl ether (MEHQ), and 0.24 parts by weight of chromium silicylate were placed in an autoclave under nitrogen atmosphere. 36 Parts by weight of ethylene oxide were added in the gas phase. The contents of the autoclave were heated to 80° C. for three hours. Ethylene oxide was removed under vacuum and the reaction mixture cooled to ambient temperature. The reaction mixture was then distilled under vacuum at 60° C. to obtain a 2-hydroxyethylmethacrylate-rich solution with a characteristic composition according to Table 3. There was a clear correlation between the purity of the methacrylic acid used and the optical properties of the hydroxyester as well as the diester content. This is relevant for the further processing of the hydroxyester, for example polymerisation for biomedical products, such as soft, oxygen-permeable contact lenses.

TABLE 3

(MAA = methacrylic acid)

|  | MAA from Example 1 | MAA from Example 1a | MAA from Example 2 | MAA from Example 3 | MAA from Example 4 | MAA from Example 4a |
|---|---|---|---|---|---|---|
| 2-Hydroxy methylmethacrylate | 98.2 wt. % | 97.2 wt. % | 98.9 wt. % | 98.4 wt. % | 98.5 wt. % | 97.9 wt. % |
| Diester (Crosslinker) | 0.6 wt. % | 0.8 wt. % | 0.3 wt. % | 0.4 wt. % | 0.5 wt. % | 0.6 wt. % |
| APHA (Pt—Co) | 5 | 12 | 3 | 4 | 3 | 5 |

Reference Numerals 1 flow
2 first reaction tube
3 second reaction tube
4 salt bath
5 gaseous crude methacrylic acid
6 quench unit
7 aqueous crude methacrylic acid
8 low boilers
9 low boilers distillation column
10 low boilers
11 aqueous crude methacrylic acid
12 extraction unit
13 crude methacrylic acid organic phase (extract)
14 distillation column (of purification unit)
15 low boilers
16 crude methacrylic acid-comprising product
17 rectification column with separating wall
18 inlet for crude methacrylic acid-comprising product
19 inhibitor/stabiliser
20 pure methacrylic acid
21 methacrylic acid head fraction
22 methacrylic acid bottom fraction
23 side outlet for pure methacrylic acid
24 inert zone
25 first oxidation catalyst
26 inert zone
27 inert zone
28 second oxidation catalyst
29 inert zone
30 quench agent recycle
31 separating wall
32 rectification column without separating wall
33 inlet for crude methacrylic acid-comprising product
34 side outlet
35 purification unit
36 reflux
37 gas phase oxidation unit
38 bottom outlet
39 separation unit
40 crystallisation unit
41 wash unit
42 melt device
43 wall of rectification column
D main flow direction of crude methacrylic acid-comprising product

The invention claimed is:

1. A process for preparation of pure methacrylic acid, comprising:

a) carrying out gas phase oxidation of a $C_4$ compound to obtain a methacrylic acid-comprising gas phase, b) condensing the methacrylic acid-comprising gas phase to obtain an aqueous methacrylic acid solution, c) separating at least a part of the methacrylic acid from the aqueous methacrylic acid solution to obtain at least one crude methacrylic acid-comprising product; and d) separating at least a part of the methacrylic acid from the at least one crude methacrylic acid-comprising product by a thermal separation process to obtain a pure methacrylic acid;

wherein said thermal separation process is a distillation or rectification;

wherein in d), the methacrylic acid is separated by rectification from at least a part of the at least one crude methacrylic acid-comprising product, wherein the pure methacrylic acid is removed in a side outlet from a column used for the rectification; and wherein the amount of pure methacrylic acid removed in a defined time interval is 40 to 80% of the amount of the amount of crude methacrylic acid-comprising product introduced into the rectification column in the same time interval.

2. The process according to claim 1, further comprising in c):

c1α) extracting the methacrylic acid from the aqueous methacrylic acid solution by an organic extraction agent to obtain an aqueous phase and an organic phase, c1β) separating at least a part of the organic extraction agent from the organic phase by at least one thermal separation process to obtain at least one methacrylic acid-comprising bottom product as the crude methacrylic acid-comprising product.

3. The process according to claim 2, wherein the organic extraction agent used in c1α) has a boiling point of less than 161° C., measured at atmospheric pressure.

4. The process according to claim 1, further comprising in c):

c2α) crystallizing at least a part of the methacrylic acid from the aqueous methacrylic acid solution, c2β) optionally, washing the crystallised methacrylic acid, and c2g) melting at least a part of the crystallised methacrylic acid to obtain at least one crude methacrylic acid-comprising product.

5. The process according to claim 1, wherein the at least one crude methacrylic acid-comprising product introduced into d) is obtained by distillation or crystallisation of a composition which comprises at most 95 wt. %, methacrylic acid.

6. The process according to claim 1, wherein the at least one crude methacrylic acid-comprising product introduced into d) is obtained by distillation or crystallisation of a composition which comprises at least 5 wt. % of a $C_4$-$C_8$ hydrocarbon.

7. The process according to claim 1, wherein the at least one crude methacrylic acid-comprising product introduced into d) has an APHA number according to DIN ISO 6271 of at least 100.

8. The process according to claim 1, wherein the rectification in d) is carried out at a bottom pressure in a range from 1 to 100 mbar.

9. The process according to claim 1, wherein the rectification in d) is carried out at a bottom temperature in a range from 40 to 200° C.

10. The process according to claim 1, wherein the rectification in d) is carried out at a bottom temperature of less than 90° C.

11. The process according to claim 1, wherein the rectification column has more than 0 and up to 10 theoretical plates per meter.

12. The process according to claim 1, wherein the pure methacrylic acid obtained in d) is removed at a height in a range between a lower fourth and an upper fourth of the rectification column.

13. The process according to claim 1, wherein the at least one crude methacrylic acid-comprising product introduced into d) is subjected to a flow resistance at or after entering into the rectification column.

14. The process according to claim 13, wherein the at least one crude methacrylic acid-comprising product entering the column impinges on the flow resistance at an angle in the range from 60° to 120°, based on a main flow direction at the flow resistance of the crude methacrylic acid-comprising product entering the column.

15. The process according to claim 1, wherein the at least one crude methacrylic acid-comprising product obtained in c) is introduced into the bottom of the rectification column.

16. The process according to claim 1, wherein the at least one crude methacrylic acid-comprising product obtained in c) is introduced into the rectification column from 1 to 5 theoretical floors below the side outlet.

17. The process according to claim 1, wherein the thermal separation in d) is carried out in the presence of a decolourisation agent.

18. The process according to claim 17, wherein the decolourisation agent is an aminoguanidinium salt.

19. The process according to claim 18, wherein the aminoguanidinium salt is aminoguanidinium bicarbonate.

20. The process according to claim 17, wherein the decolourisation agent is added
   A) to the at least one crude methacrylic acid-comprising product obtained in c) before the thermal separation in d), or
   B) during the thermal separation in d).

21. The process according to claim 1, wherein in d), less than 5 wt. %, impurities different from methacrylic acid are precipitated from the at least one crude methacrylic acid-comprising product obtained in c).

22. The process according to claim 1, wherein at least d) is carried out continuously.

23. The process according to claim 1, wherein the process is carried out in a device, wherein the device comprises at least the following components in fluid-conducting communication with each other:
   a1) a gas phase oxidation unit;
   b1) an absorption unit;
   c1) a separation unit; and
   d1) a purification unit;
   wherein the purification unit comprises at least one distillation column and the at least one distillation column comprises at least one side outlet for pure methacrylic acid.

24. A process for preparation of methacrylic acid esters, comprising
   A) preparing pure methacrylic acid by a process according to claim 1, and
   B) esterifying the pure methacrylic acid.

25. A process for preparation of a polymethacrylate, comprising
   i) preparing pure methacrylic acid by a process according to claim 1, and
   ii) carrying out radical polymerisation of the pure methacrylic acid, optionally in the presence of monomers which are co-polymerisable with methacrylic acid.

26. A process for preparation of a polymethacrylic acid ester, comprising
   i) preparing a methacrylic acid ester by a process according to claim 24, and
   ii) carrying out radical polymerisation of the methacrylic acid ester, optionally in the presence of monomers which are co-polymerisable with methacrylic acid esters.

27. The process of claim 1, wherein said pure methacrylic acid is a methacrylic acid which comprises less than 1 wt. % impurities, based on the total weight of methacrylic acid and impurities.

28. The process of claim 1, wherein said pure methacrylic acid is a methacrylic acid which comprises less than 0.8 wt. % impurities, based on the total weight of methacrylic acid and impurities.

29. The process of claim 1, wherein said pure methacrylic acid is a methacrylic acid which comprises less than 0.5 wt. % impurities, based on the total weight of methacrylic acid and impurities.

30. The process of claim 1, wherein said pure methacrylic acid is a methacrylic acid which comprises less than 0.3 wt. % impurities, based on the total weight of methacrylic acid and impurities.

* * * * *